United States Patent [19]

Murahashi et al.

[11] Patent Number: 5,405,974
[45] Date of Patent: Apr. 11, 1995

[54] PROCESS FOR PRODUCING A LACTONE OR AN ESTER

[75] Inventors: Shun-Ichi Murahashi, Ikeda; Yoshiaki Oda, Toyonaka, both of Japan

[73] Assignee: Sumitomo Chemical Company, Limited, Osaka, Japan

[21] Appl. No.: 995,895

[22] Filed: Dec. 23, 1992

[30] Foreign Application Priority Data

Dec. 25, 1991 [JP] Japan .................................. 3-342855
Mar. 11, 1992 [JP] Japan .................................. 4-052440

[51] Int. Cl.⁶ ..................... C07D 313/00; C07C 69/76
[52] U.S. Cl. ..................... 549/266; 549/273; 549/295; 554/124; 560/61; 560/129; 560/179; 560/205
[58] Field of Search ............... 549/273, 266, 295; 554/124; 560/129, 179, 210, 61, 205

[56] References Cited

U.S. PATENT DOCUMENTS

3,025,306  3/1962  Guest et al. ........................ 549/272
3,483,222 12/1969  Sennewald et al. ................ 549/272

FOREIGN PATENT DOCUMENTS

46-12456   3/1971  Japan .
56-14095   4/1977  Japan .
52-100403  8/1977  Japan .
1009773   11/1965  United Kingdom .
1061700    3/1967  United Kingdom .
1103885    2/1968  United Kingdom .
1245500    9/1971  United Kingdom .

OTHER PUBLICATIONS

Yamada et al., "The Baeyer–Villiger Oxidation of Ketones Catalyzed by Nickel(II) Complexes with Combined Use of Molecular Oxygen and an Aldehyde," Chemistry Letters, 641–44 (1991).
Chemical Abstracts, 65: 20019a (1966).

*Primary Examiner*—C. Warren Ivy
*Attorney, Agent, or Firm*—Cushman, Darby & Cushman

[57] ABSTRACT

A process for producing a lactone or an ester represented by the following general formula (2), wherein $R^1$ and $R^2$, identical or different, each represents ($C_1$—$C_{20}$) alkyl group; alkyl group substituted with a terminal alkenyl, halogen, alkoxy, phenoxy or acyloxy; phenyl group; or phenyl group substituted with alkyl, halogen, alkoxy, phenoxy or acyloxy; phenylalkyl group; or phenylalkyl group substituted with alkyl, halogen, alkoxy, phenoxy or acyloxy; provided that when $R^1$ and $R^2$, identical or different, each represents unsubstituted alkyl group or alkyl group substituted with a terminal alkenyl, halogen, alkoxy, phenoxy, acyloxy or phenyl, the respective alkyl parts of $R^1$ and $R^2$ may be conjunct to each other; which comprises reacting a ketone represented by the following general formula (1), wherein $R^1$ and $R^2$ are as defined above, with oxygen in the presence of an aldehyde either in the absence of catalyst or in the presence of a heterogeneous iron-containing or ruthenium-containing catalyst:

$$R^1-\underset{\underset{O}{\|}}{C}-R^2 \quad (1)$$

$$R^1-\underset{\underset{O}{\|}}{C}-O-R^2 \quad (2)$$

9 Claims, No Drawings

PROCESS FOR PRODUCING A LACTONE OR AN ESTER

BACKGROUND OF THE INVENTION

1. Field of the Invention

This invention relates to a process for producing a lactone or an ester by oxidation of a ketone.

The above-mentioned lactone and ester are useful as sythetic intermediates in the production of various products including pharmaceuticals, pesticides, perfumes, liquid crystals, resins, pheromones, etc. Among them, $\epsilon$-caprolactone is particularly important as a synthetic intermediate of the polyester used as a starting material of urethane polymers.

2. Related Art

A process for producing a lactone or an ester by the oxidation of a ketone using a peracid such as peracetic acid, m-chloroperbenzoic acid and the like is well known, as disclosed in Some Modern Methods of Organic Sybthesis, 3rd ed., pp. 403–407). However, the process cannot be said to be advantageous from the industrial point of view, because peracids are high in shock sensitivity and explosive.

With the aim of solving this problem, there have been developed a number of processes which comprise oxidizing a cyclic ketone in the presence of an aldehyde with various metallic catalysts (U.S. Pat. No. 3,025,306), with a soluble iron catalyst such as FeCl$_3$, Fe(OAc)$_3$, Fe(acac)$_3$ and the like (U.S Pat. No. 3,483,222), with a soluble nickel catalyst (Japanese Patent Application KOKOKU No. 46-12456), or with soluble palladium, vanadium, molybdenum, tungsten or cerium catalyst (Japanese Patent Application KOKOKU No. 56-14095).

However, none of these processes can be said to be advantageous industrially because of low conversion and low selectivity. Apart from them, an improved process using a 1,3-diketonatonickel catalyst has been developed recently (Chem. Lett., 1991, 641). However, this process uses a homogeneous catalyst which makes troublesome the procedure for separating and recovering the catalyst from the objective product, i.e. lactone or ester, and therefore this process, too, cannot be said to be satisfactory from the industrial viewpoint.

SUMMARY OF THE INVENTION

It is an object of the present invention to provide a process for advantageously producing a lactone or an ester by oxidizing a ketone without use of catalyst or by the use of a readily available and recoverable catalyst.

With the aim of solving the problems mentioned above, the present inventors conducted various studies to attain this invention.

Thus, according to the present invention, there is provided a process for producing a lactone or an ester represented by the following general formula (2):

wherein R$^1$ and R$^2$, identical or different, each represents (C$_1$—C$_{20}$) alkyl group; alkyl group substituted with a terminal alkenyl, halogen, alkoxy, phenoxy or acyloxy; phenyl group; or phenyl group substituted with alkyl, halogen, alkoxy, phenoxy or acyloxy; phenylalkyl group; or phenylalkyl group substituted with alkyl, halogen, alkoxy, phenoxy or acyloxy; provided that when R$^1$ and R$^2$, identical or different, each represents unsubstituted alkyl group or alkyl group substituted with a terminal alkenyl, halogen, alkoxy, phenoxy, acyloxy or phenyl, the respective alkyl parts of R$^1$ and R$^2$ may be conjunct to each other; which comprises reacting a ketone represented by the following general formula (1):

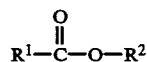

wherein R$^1$ and R$^2$ are as defined above, with oxygen in the presence of an aldehyde either in the absence of catalyst or in the presence of a heterogeneous iron-containing or ruthenium-containing catalyst.

DETAILED DESCRIPTION OF THE INVENTION

Examples of the ketone represented by formula (1) which can be used as a starting material in this invention include acetone, 2-butanone, 3-methyl-2-butanone, pinacolone, 2-pentanone, 3-pentanone, 2-hexanone, 3-hexanone, 2-heptanone, 3-heptanone, 4-heptanone, 2,2-dimethyl-6-hepten-3-one, 1-chloro-3,3-dimethyl-2-butanone, 3,3-dimethyl-1-methoxy-2-butanone, 3,3-dimethyl-1-phenoxy-2-butanone, 1-acetoxy-3,3-dimethyl-2-butanone, cyclobutanone, cyclopentanone, cyclohexanone, cycloheptanone, cyclooctanone, cyclododecanone, 2-methylcyclobutanone, 2-octylcyclobutanone, 2-methylcyclopentanone, 3-methylcyclopentanone, 2-hexylcyclopentanone, 2-undecylcyclopentanone, 2,5-dimethylcyclopentanone, 2-methylcyclohexanone, 3-methylcyclohexanone, 4-methylcyclohexanone, 4-t-butylcyclohexanone, 4-phenylcyclohexanone, 2-allylcyclohexanone, 2-chlorocyclohexanone, 4-methoxycyclohexanone, 4-phenoxycyclohexanone, 4-acetoxycyclohexanone, phenylacetone, acetophenone, 4'-methylacetophenone, 4'-chloroacetophenone, 4'-methoxyacetophenone, 3'-methoxyacetophenone, 2'-methoxyacetophenone, 4'-phenoxyacetophenone, 4'-acetoxyacetophenone, propiophenone, 4'-methoxypropiophenone, 1-(p-tolyl)-2-propanone, 1-(p-chlorophenyl)-2-propanone, 1-(p-methoxyphenyl)-2-propanone, 1-(p-phenoxyphenyl)-2-propanone, 1-(p-acetoxyphenyl)-2-propanone, benzophenone, 3$\alpha$-acetoxyandrostan-17-one, 3$\beta$-acetoxyandrostan-17-one, 3$\alpha$-benzoyloxyandrostan-17-one and the like.

Examples of the lactone and ester represented by general formula (2) which can be obtained according to this invention include methyl acetate, ethyl acetate, isopropyl acetate, t-butyl acetate, n-propyl acetate, ethyl propionate, n-butyl acetate, n-propyl propionate, ethyl butyrate, pentyl acetate, butyl propionate, ethyl valerate, n-propyl butyrate, t-butyl 4-pentenoate, t-butyl chloroacetate, t-butyl methoxyacetate, t-butyl phenoxyacetate, t-butyl acetoxyacetate, $\gamma$-butyrolactone, $\delta$-valerolactone, $\epsilon$-caprolactone, 7-heptanolactone, 8-octanolactone, 12-dodecanolactone, 4-methyl-4-butanolactone, 4-octyl-4-butanolactone, 5-methyl-5-pentanolactone, 4-methyl-5-pentanolactone, 5-hexyl-5-pentanolactone, 5-undecyl-5-pentanolactone, 2,5-dimethyl-5-pentanolactone, 6-methyl-6-hexanolactone, 5-methyl-6-hexanolactone, 4-methyl-6-hexanolactone, 4-t-butyl-6-hexanolactone, 4-phenyl-6-hexanolactone, 6-allyl-6-hexanolactone, 6-chloro-6-hexanolactone, 4-methoxy-6-hexanolactone, 4-phenoxy-6-hexanolactone, 4-acetoxy-6-hexanolactone, benzyl acetate, phenyl acetate, p-tolyl acetate, p-chlorophenyl acetate, p-methoxyphenyl acetate, m-methoxyphenyl acetate, o-methoxyphenyl acetate, p-phenoxyphenyl acetate, p-acetoxyphenyl acetate, phenyl propionate, ethyl benzoate, p-methoxyphenyl propionate, 4'-methylbenzyl acetate, 4'-chlorobenzyl acetate, 4'-methoxybenzyl acetate, 4'-phenoxybenzyl acetate, 4'-acetoxybenzyl acetate, phenyl benzoate, 3α-acetoxy-D-homo-17a-oxaandrostan-17-one, 3β-acetoxy-D-homo-17a-oxaandrostan-17-one, 3α-benzoyloxy-D-homo-17a-oxaandrostan-17-one and the like.

Examples of the iron-containing catalyst include Fe, $FeSO_4 \cdot 7H_2O$, $Fe_2O_3$ and the like; and examples of the ruthenium-containing catalyst include Ru-C, $RuO_2$ and the like. Among these catalysts, $FeSO_4 \cdot 7H_2O$, $Fe_2O_3$, Ru-C and $RuO_2$ are preferable, and $FeSO_4 \cdot 7H_2O$ and $Fe_2O_3$ are particularly preferable.

Mixtures of these catalysts are also usable, and these catalysts supported on heteropolyacids, silica gel, polymers and the like are also usable.

Although the amount of the catalyst is not critical, it is usually used in an amount of 0.01–120% by mole, preferably 0.1–10% by mole, based on the starting ketone.

The aldehydes which can be used in this invention include formaldehyde, acetaldehyde, propionaldehyde, butanal, pentanal, hexanal, heptanal, decanal, 2-methylpropanal, 2-methylbutanal, cyclohexanecarboxaldehyde, isovaleraldehyde, benzaldehyde, p-chlorobenzaldehyde, m-chlorobenzaldehyde, p-tolualdehyde, p-anisaldehyde, pivalaldehyde and the like. Although the amount of the aldehyde is not critical, it is usually used in an amount of 1–30 moles, preferably 1–10 moles, per mole of the ketone.

A solvent may be used in this invention. The solvents which can be used include halogenated hydrocarbons such as dichloromethane, chloroform, ethylene dichloride and the like, esters such as ethyl acetate and the like, nitriles such as acetonitrile and the like, and aromatic hydrocarbons such as benzene, toluene, xylene, monochlorobenzene, dichlorobenzene and the like.

The oxygen used in this invention is not limited to oxygen itself, but air is also usable as an oxygen. Although the method for feeding the oxygen is not critical, a method of blowing oxygen, a method of carrying out the reaction in an atmosphere of oxygen, etc. can be referred to as examples of the method. The oxygen may be either an oxygen of ordinary pressure or an oxygen of elevated pressure.

The reaction temperature is usually in the range of 0° C. to the reflux temperature of reaction mixture. Preferably, it is in the range of 20° C. to 80° C.

The reaction time is not critical particularly, and the time when the formation of the objective lactone or ester has reached a ceiling value may be taken as an end point. It is usually in the range of one hour to one week.

According to this invention, the used aldehyde is converted to the corresponding carboxylic acid which can easily be separated from the formed objective product.

After completion of the reaction, the catalyst is recovered, for example, by filtration and the filtrate is washed with an aqueous solution of sodium hydrogen sulfite and an aqueous solution of sodium hydrogen carbonate and subsequently it is concentrated and, if desired, subjected to rectification or the like, whereby the objective lactone or ester can be obtained.

According to this invention, a lactone or an ester can be obtained from a ketone and oxygen in the presence of an aldehyde without using catalyst or by using a readily available and recoverable iron-containing or ruthenium-containing catalyst. Thus, the process of this invention is quite excellent industrially.

Next, this invention will be explained in more detail with reference to the following examples. This invention is by no means limited by these examples.

EXAMPLE 1

A mixture of 168 mg of cyclpentanone, 637 mg of benzaldehyde and 12 ml of benzene was vigorously stirred under an oxygen atmosphere at 25° C. for 48 hours. Analysis of the reaction mixture by gas chromatography (GC) showed that δ-valerolactone had been formed in 92% yield.

EXAMPLE 2

A mixture of 196 mg of cyclohexanone, 637 mg of benzaldehyde and 12 ml of benzene was vigorously stirred under an oxygen atmosphere at 25° C. for 48 hours. Analysis of the reaction mixture by GC showed that ε-caprolactone had been formed in 97% yield.

EXAMPLE 3

A mixture of 224 mg of 2-methylcyclohexanone, 637 mg of benzaldehyde and 12 ml of benzene was vigorously stirred under an oxygen atmosphere at 25° C. for 48 hours. Analysis of the reaction mixture by GC showed that 6-methyl-6-hexanolactone had been formed in 95% yield.

EXAMPLE 4

A mixture of 300 mg of 4'-methoxyacetophenone, 637 mg of benzaldehyde and 12 ml of benzene was vigorously stirred under an oxygen atmosphere at 25° C. for 48 hours. Analysis of the reaction mixture by GC showed that p-methoxyphenyl acetate had been formed in 94% yield.

EXAMPLE 5

A mixture of 309 mg of 4-t-butylcyclohexanone, 258 mg of pivalaldehyde and 12 ml of dichloromethane was vigorously stirred under an oxygen atmosphere at 25° C. for 48 hours. Analysis of the reaction mixture by GC showed that 4-t-butyl-6-hexanolactone had been formed in 90% yield.

EXAMPLES 6–10

Mixtures of 168 mg of cyclopentanone, 1% by mole, based on the cyclopentanone, of a catalyst (varied) shown in Table 1, 849 mg of benzaldehyde and 12 ml of dichloromethane were vigorously stirred under an oxygen atmosphere at 25° C. for 17 hours. Analysis of the reaction mixtures by GC gave the results shown in Table 1. the products were quantitatively analyzed by the GC-IS (internal standard) method, and their structures were identified by the GC-MS (mass pectrum) method.

TABLE 1

| Example No. | Catalyst | Conversion (%) *1 | Yield of δ-valerolactone *2 |
|---|---|---|---|
| 6 | Fe | 14 | 9 (61) |
| 7 | $FeSO_4 \cdot 7H_2O$ | 77 | 41 (53) |
| 8 | $Fe_2O_3$ | 76 | 43 (56) |
| 9 | 5% Ru—C | 35 | 26 (75) |

TABLE 1-continued

| Example No. | Catalyst | Conversion (%) *1 | Yield of δ-valerolactone *2 |
| --- | --- | --- | --- |
| 10 | RuO$_2$ | 51 | 33 (65) |

*1 Based on cyclopentanone
*2 Based on cyclopentanone
The figures shown in ( ) denote yields based on the consumed cyclopentanone.

EXAMPLES 11–16

Mixtures of 168 mg of cyclopentanone, 3.2 mg of Fe$_2$O$_3$, 4 equivalents, based on the cyclopentanone, of an aldehyde (varied) shown in Table 2 and 12 ml of dichloromethane were stirred under an oxygen atmosphere at 25° C. for 17 hours. Analysis of the reaction mixtures by GC gave the results shown in Table 2.

TABLE 2

| Example No. | Aldehyde | Conversion (%) *1 | Yield of δ-valerolactone (%) *2 |
| --- | --- | --- | --- |
| 11 | Acetaldehyde | 37 | 9 (23) |
| 12 | Heptanal | — | 7 (—) |
| 13 | 2-Methylpropanal | 12 | 4 (35) |
| 14 | Cyclohexanecarboxaldehyde | 12 | 11 (93) |
| 15 | Isovaleraldehyde | 26 | 20 (80) |
| 16 | m-Chlorobenzaldehyde | 11 | 9 (81) |

*1 Based on cyclopentanone
*2 Based on cyclopentanone
The figures shown in ( ) denote yields based on the consumed cyclopentanone.

EXAMPLES 17–22

Mixtures of 168 mg of cyclopentanone, 3.2 mg of Fe$_2$O$_3$, 3 equivalents, based on the cyclopentanone, of an aldehyde (varied) shown in Table 3 and 12 ml of benzene were stirred under an oxygen atmosphere at 25° C. for 17 hours. Analysis of the reaction mixtures by GC gave the results shown in Table 3.

TABLE 3

| Example No. | Aldehyde | Conversion (%) *1 | Yield of δ-valerolactone (%) *2 |
| --- | --- | --- | --- |
| 17 | Benzaldehyde | 83 | 81 (98) |
| 18 | Acetaldehyde | 4 | 4 (100) |
| 19 | Propionaldehyde | 40 | 40 (100) |
| 20 | Heptanal | 53 | 53 (100) |
| 21 | 2-Methylpropanal | 41 | 41 (100) |
| 22 | Pivalaldehyde | 34 | 34 (100) |

*1 Based on cyclopentanone
*2 Based on cyclopentanone
The figures shown in ( ) denote yields based on the consumed cyclopentanone

EXAMPLES 23–25

Mixtures of 168 mg of cyclopentanone, 3.2 mg of Fe$_2$O$_3$, 849 mg of benzaldehyde and 12 ml of a solvent (varies) shown in Table 4 were stirred under an oxygen atmosphere at 25° C. for 17 hours. Analysis of the reaction mixtures by GC gave the results shown in Table 4.

TABLE 4

| Example No. | Solvent | Conversion (%) *1 | Yield of δ-valerolactone (%) *2 |
| --- | --- | --- | --- |
| 23 | Toluene | 83 | 80 (96) |
| 24 | Ethyl acetate | 49 | 47 (96) |
| 25 | Acetonitrile | 25 | 23 (91) |

*1 Based on cyclopentanone
*2 Based on cyclopentanone
The figures shown in ( ) denote yields based on the consumed cyclopentanone.

EXAMPLES 26–28

Mixtures of 168 mg of cyclopentanone, 3.2 mg of Fe$_2$O$_3$, a varied amount (shown in Table 5) of benzaldehyde and 12 ml of benzene were stirred under an oxygen atmosphere at 25° C. for 17 hours. Analysis of the reaction mixtures by GC gave the results shown in Table 5.

TABLE 5

| Example No. | Amount of benzaldehyde used (equivalents based on cyclopentanone) | Conversion (%) *1 | Yield of δ-valerolactone (%) *2 |
| --- | --- | --- | --- |
| 26 | 1 | 28 | 29 (101) |
| 27 | 2 | 41 | 40 (98) |
| 28 | 3 | 83 | 81 (98) |

*1 Based on cyclopentanone
*2 Based on cyclopentanone
The figures shown in ( ) denote yields based on the consumed cyclopentanone.

EXAMPLES 29–32

Mixtures of 168 mg of cyclopentanone, a varied amount (shown in Table 6) of Fe$_2$O$_3$, 637 mg of benzaldehyde and 12 ml of benzene were stirred under an oxygen atmosphere at 25° C. for 17 hours. Analysis of the reaction mixtures by GC gave the results shown in Table 6.

TABLE 6

| Example No. | Amount of Fe$_2$O$_3$ (equivalent) based on cyclopentanone | Conversion (%) *1 | Yield of δ-valerolactone (%) *2 | Turnover number |
| --- | --- | --- | --- | --- |
| 29 | 0.001 | 67 | 64 (94) | 635 |
| 30 | 0.005 | 58 | 54 (93) | 108 |
| 31 | 0.05 | 86 | 80 (93) | 16 |
| 32 | 0.10 | 94 | 85 (90) | 8.5 |

*1 Based on cyclopentanone
*2 Based on cyclopentanone
The figures shown in ( ) denote yields based on the consumed cyclopentanone.

EXAMPLES 33–44

Mixtures of 2 millimoles of a ketone (varied) shown in Table 7, 3.2 mg of Fe$_2$O$_3$, 637 mg of benzaldehyde and 12 ml of benzene were stirred under an oxygen atmosphere at 25° C. for 17 hours. Analysis of the reaction mixtures by GC gave the results shown in Table 7. The products were quantitatively analyzed by the GC-IS method, and their structures were identified by GC-MS.

In isolating the products, each of the reaction mixtures was washed with a saturated aqueous solution of sodium hydrogen carbonate and dried with sodium sulfate, the organic layer was concentrated, and the residue thus obtained was purified by silica gel column chromatography or preparative thin layer chromatography.

TABLE 7

| Example No. | Ketone | Conversion (%) *1 | Product | Yield (%) *2 |
|---|---|---|---|---|
| 33 | Cyclobutanone | 85 | γ-Butyrolactone | 84 (99) [81] |
| 34 | Cyclohexanone | 97 | ε-Caprolactone | 95 (98) [92] |
| 35 | Cycloheptanone | 11 | 7-Heptanolactone | 11 (100) |
| 36 | 2-Methylcyclohexanone | 83 | 6-Methyl-6-hexanolactone | 80 (97) [78] |
| 37 | 4-Methylcyclohexanone | 97 | 4-Methyl-6-hexanolactone | 97 (100) [93] |
| 38 | 2-Heptanone | 5 | Pentyl acetate | 5 (100) |
| 39 | Pinacolone | 40 | t-Butyl acetate | 40 (100) |
| 40 | 4'-Methoxyacetophenone | 80 | p-Methoxyphenyl acetate | 80 (100) [77] |
| 41 | Acetophenone | 5 | Phenyl acetate | 5 (100) |
| 42 | Propiophenone | 8 | Phenyl propionate | 6 (80) |
|  |  |  | Ethyl benzoate | 2 (20) |
| 43 | 2-Allylcyclohexanone | — | 6-Allyl-6-hexanolactone | [63] |
| 44 | 3β-Acetoxyandrostan-17-one | — | 3β-Acetoxy-D-homo-17-a-oxaandrostan-17-one | [56] |

*1 Based on ketone
*2 Based on ketone
The figures shown in ( ) denote yields based on the consumed ketone.
The figures shown in [ ] denote isolated yields.

What is claimed is:

1. A process for producing a lactone or an ester represented by the following general formula (2):

$$R^1-\overset{O}{\underset{\|}{C}}-O-R^2 \quad (2)$$

wherein $R^1$ and $R^2$, identical or different each represents ($C_1$—$C_{20}$) alkyl group; alkyl group substituted with a terminal alkenyl, halogen, alkoxy, phenoxy or acyloxy; phenyl group; or phenyl group substituted with alkyl, halogen, alkoxy, phenoxy or acyloxy; phenylalkyl group; or phenylalkyl group substituted with alkyl, halogen, alkoxy, phenoxy or acyloxy; provided that when $R^1$ and $R^2$, identical or different, each represents unsubstituted alkyl group or alkyl group or alkyl group substituted with a terminal alkenyl, halogen, alkoxy, phenoxy, acyloxy or phenyl, the respective alkyl parts of $R^1$ and $R^2$ may be conjunct to each other; which comprises reacting a ketone represented by the following general formula (1):

$$R^1-\overset{O}{\underset{\|}{C}}-R^2 \quad (1)$$

wherein $R^1$ and $R^2$ are as defined above, with oxygen in the presence of an aromatic aldehyde and, as a solvent, an aromatic hydrocarbon.

2. A process for producing a lactone or an ester represented by the following general formula (2):

$$R^1-\overset{O}{\underset{\|}{C}}-O-R^2 \quad (2)$$

wherein $R^1$ and $R^2$ identical or different, each represents ($C_1$—$C_{20}$) alkyl group; alkyl group substituted with a terminal alkenyl, halogen, alkoxy, phenoxy or acyloxy; phenyl group; or phenyl group substituted with alkyl, halogen, alkoxy, phenoxy or acyloxy; phenylalkyl group; or phenylalkyl group substituted with alkyl, halogen, alkoxy, phenoxy or acyloxy; provided that when $R^1$ and $R^2$, identical or different, each represents unsubstituted alkyl group or alkyl group or alkyl group substituted with a terminal alkenyl, halogen, alkoxy, phenoxy, acyloxy or phenyl, the respective alkyl parts of $R^1$ and $R^2$ may be conjunct to each other; which comprises reacting a ketone represented by the following general formula (1):

$$R^1-\overset{O}{\underset{\|}{C}}-R^2 \quad (1)$$

wherein $R^1$ and $R^2$ are as defined above, with oxygen in the presence of an aromatic aldehyde, an aromatic hydrocarbon as a solvent, and ferric oxide.

3. A process according to claim 2, wherein the catalyst is used in an amount of 0.01 to 120% by mole based on the starting ketone.

4. A process according to claim 1 or 2, wherein the aromatic aldehyde is benzaldehyde, p-chlorobenzaldehyde, m-chlorobenzaldehyde, p-tolualdehyde, or p-anisaldehyde.

5. A process according to claim 1 or 2, wherein the alderhyde is used in an amount of 1 to 30 moles per mole of the ketone.

6. A process according to claim 1 or 2, wherein the oxygen is oxygen itself or air.

7. A process according to claim 1 or 2, wherein the reaction is carried out at a temperature of 0° C. to the reflux temperature of the reaction mixture.

8. A process according to claim 1 or 2, wherein the reaction is carried out for one hour to one week.

9. A process according to claim 1 or 2, wherein the aromatic hydrocarbon is benzene, toluene, xylene, monochlorobenzene or dichlorobenzene.

* * * * *